United States Patent
Hayashi et al.

(10) Patent No.: US 10,962,495 B2
(45) Date of Patent: Mar. 30, 2021

(54) BLOOD COAGULATION SYSTEM ANALYSIS SYSTEM, BLOOD COAGULATION SYSTEM ANALYSIS METHOD, AND BLOOD COAGULATION SYSTEM ANALYSIS PROGRAM

(71) Applicant: Sony Corporation, Tokyo (JP)

(72) Inventors: Yoshihito Hayashi, Chiba (JP); Marcaurele Brun, Tokyo (JP); Kenzo Machida, Kanagawa (JP); Aya Murata, Kanagawa (JP); Shinji Omori, Chiba (JP); Seungmin Lee, Kanagawa (JP); Kaori Kawaguchi, Saitama (JP)

(73) Assignee: Sony Corporation, Tokyo (JP)

( * ) Notice: Subject to any disclaimer, the term of this patent is extended or adjusted under 35 U.S.C. 154(b) by 256 days.

(21) Appl. No.: 16/087,438

(22) PCT Filed: Feb. 17, 2017

(86) PCT No.: PCT/JP2017/005861
§ 371 (c)(1),
(2) Date: Sep. 21, 2018

(87) PCT Pub. No.: WO2017/169261
PCT Pub. Date: Oct. 5, 2017

(65) Prior Publication Data
US 2019/0162690 A1 May 30, 2019

(30) Foreign Application Priority Data

Mar. 29, 2016 (JP) .............. JP2016-066056

(51) Int. Cl.
*G01N 33/86* (2006.01)
*G01N 27/22* (2006.01)
*G01N 33/49* (2006.01)

(52) U.S. Cl.
CPC ....... *G01N 27/221* (2013.01); *G01N 33/4905* (2013.01); *G01N 33/86* (2013.01); *G01N 2333/75* (2013.01)

(58) Field of Classification Search
CPC .. G01N 27/221; G01N 33/4905; G01N 33/86; G01N 2333/75
See application file for complete search history.

(56) References Cited

U.S. PATENT DOCUMENTS

| 2005/0015001 A1* | 1/2005 | Lec .................. A61B 8/12 600/369 |
| 2015/0077144 A1 | 3/2015 | Hayashi et al. |
| 2017/0030891 A1 | 2/2017 | Brun et al. |

FOREIGN PATENT DOCUMENTS

| EP | 3133390 A1 | 2/2017 |
| JP | 2010-181400 A | 8/2010 |

(Continued)

OTHER PUBLICATIONS

Written Opinion and English translation thereof dated Apr. 4, 2017 in connection with International Application No. PCT/JP2017/005861.

(Continued)

*Primary Examiner* — Jennifer Wecker
*Assistant Examiner* — Michael Paul Shimek
(74) *Attorney, Agent, or Firm* — Wolf, Greenfield & Sacks, P.C.

(57) ABSTRACT

To provide a system capable of evaluating a deficiency and/or a lowered function of extrinsic coagulation factors or intrinsic coagulation factors with high sensitivity by adding new procedures and apparatuses to a blood coagulation system analysis procedure, an apparatus, or the like.
A blood coagulation system analysis system includes a blood coagulation system measurement apparatus that performs blood coagulation system measurement of a blood (Continued)

sample; and a blood coagulation system analysis apparatus including a coagulation parameter extraction unit that extracts a coagulation parameter from a measurement result by the blood coagulation system measurement apparatus, and a blood coagulation evaluation unit that evaluates a level of blood coagulation of the blood sample on the basis of the coagulation parameter, the measurement by the blood coagulation system measurement apparatus being performed under an extrinsic system acceleration condition and an intrinsic system acceleration condition.

12 Claims, 11 Drawing Sheets

(56) References Cited

FOREIGN PATENT DOCUMENTS

| | | |
|---|---|---|
| JP | 2012-194087 A | 10/2012 |
| JP | 2013-221782 A | 10/2013 |
| WO | WO 2013/153735 A1 | 10/2013 |
| WO | WO 2015/159623 A1 | 10/2015 |

OTHER PUBLICATIONS

International Preliminary Report on Patentability and English translation thereof dated Oct. 11, 2018 in connection with International Application No. PCT/JP2017/005861.

International Search Report and English translation thereof dated Apr. 4, 2017 in connection with International Application No. PCT/JP2017/005861.

Hayashi et al., Principles of Dielectric Blood Coagulometry as a Comprehensive Coagulation Test, Anal. Chem., 2015, vol. 87, pp. 10072-10079.

No Author Listed, TEG6s Ketsueki Gyoko Bunseki Sochi [TEG6s Hemostasis analyzer system], Aug. 27, 2015 http://reg.haemonetics.com/~/media/Sharepoint/Devices/TEG/Marketing/Brochures/TEG6s_Brochure/COL-COPY-000918-JA_Brochure_TEG6s.pdf.pdf, retrieved Aug. 31, 2018, 8p (1 page translation).

* cited by examiner

BLOOD COAGULATION SYSTEM ANALYSIS SYSTEM, BLOOD COAGULATION SYSTEM ANALYSIS METHOD, AND BLOOD COAGULATION SYSTEM ANALYSIS PROGRAM

CROSS-REFERENCE TO RELATED APPLICATIONS

This application claims the benefit under 35 U.S.C. § 371 as a U.S. National Stage Entry of International Application No. PCT/JP2017/005861, filed in the Japanese Patent Office as a Receiving Office on Feb. 17, 2017, which claims priority to Japanese Patent Application Number JP2016-066056, filed in the Japanese Patent Office on Mar. 29, 2016, each of which is hereby incorporated by reference in its entirety.

TECHNICAL FIELD

The present invention relates to a blood coagulation system analysis system, a blood coagulation system analysis method, and a blood coagulation system analysis program.

BACKGROUND ART

Thrombus formation (coagulation) and dissolution (fibrinolysis) in vivo proceed in a complex cascade reaction. The reaction is associated with both of a number of molecular components including coagulation factors, fibrinogen, fibrin, and the like and cell components such as vascular endothelial cells, platelets, and the like.

In treatment or prevention of coagulation- and fibrinolysis-related disease and injury, a variety of tests are performed to determine a blood coagulation ability and a fibrinolysis ability of a patient. The coagulation and fibrinolysis tests can be roughly classified into a quantitative test that measures amounts of specific molecules involved in a coagulation and fibrinolysis reaction system such as a variety of coagulation factors, fibrinogen, and D-dimers, and a functional test that evaluates a functional level of an entire reaction system or a part thereof.

The coagulation reaction system is separated into a mechanism (extrinsic system) that starts with complex formation of a tissue factor and an activated coagulation VII factor and a mechanism (intrinsic system) that starts with activation of a XII factor owing to a contact with a foreign matter or the like. The both merge at a stage of activation of an X factor.

Note that, in accordance with practices of a thrombus hemostasis field, the coagulation factor is expressed by adding "F" to the top of the Roman number of the factor number and, if the factor is activated, by adding "a" to the end. For example, a XII factor and an activated VII factor are expressed as FXII and FVIIa, respectively.

The generated FXa activates prothrombin (FII) and converts it into thrombin (FIIa). By an action of thrombin, fibrinogen is converted into fibrin. The generated fibrin is polymerized each other and forms a three-dimensional network structure called insoluble stable fibrin by a further action of FXIIIa. A thrombus (blood clot) is a structure formed of the network structure into which red blood cells are mainly entangled. Also, platelets contribute to the structure formation. Once the thrombus is formed, a fibrinolysis reaction system begins to work in order to prevent solidification from excessively accelerating. The thrombus finished to serve as hemostasis is dissolved eventually.

As function tests of an extrinsic coagulation ability and an intrinsic coagulation ability, a prothrombin time (PT) and an activated partial thromboplastin time (APTT) are widely used. In these tests, substances (e.g., a tissue factor and ellagic acid) that elicit extrinsic and intrinsic coagulation reactions are extra-excessively added, so that test results are obtained in a short time. Normal values of a prothrombin time and an activated partial thromboplastin time are each approximately 10 seconds and 30-40 seconds. Accordingly, these tests are suitable to evaluate a significant decrease of a coagulation ability, i.e. a bleeding tendency, but are unsuitable to evaluate a significant increase of the coagulation ability, i.e., a thrombus tendency or a subtle change of the coagulation ability. In addition, the test is performed by using plasma obtained by centrifuging blood samples. Because cell components such as platelets and red blood cells that play important roles in the coagulation reaction in vivo are removed by centrifugation, the test result is often inconsistent with an actual clinical condition.

As another function tests, there are thromboelastography and thromboelastograph cytometry. Specifically, a TEG 5000 (registered trademark, Hemonetics Corporation) and a ROTEM delta (registered trademark, Tim Innovations) are practically used.

In the TEG 5000, whole blood samples are injected into a measurement container, a cup, eliciting substances to serve the test purpose are added, a rod-like pin hanging by wire from a top of a container is immersed, and a steady reciprocating angular motion (typically back and forth motion in a 4.45 degrees range for 10 seconds) is applied to the container. As the coagulation reaction proceeds, viscoelasticity of the samples is increased, the relative motion of the cup and the pin is decreased, and a rotational displacement of the pin is thus increased. The rotational displacement is recorded over time by using an optical system of an apparatus. As a result, the waveform called thromboelastogram is obtained. Although there is a difference that the reciprocating angular motion is given not to the cup but to the pin, the ROTEM delta is also basically based on the same principle. Whereas the prothrombin time and the activated partial thromboplastin time are coagulation end point detection methods, the thromboelastography or the thromboelastography cytometry can advantageously monitor over time a series of processes from solidification starting to thrombus formation and subsequent fibrinolysis by one apparatus.

It can be said that the thromboelastography or the thromboelastography cytometry comprehensively tests work of the entire reaction system until fibrin generation by focusing on the fibrin generation that is the final stage of the coagulation cascade reaction and by monitoring the processes of the network formation (coagulation) and the dissolution (fibrinolysis) through the viscoelasticity of the samples.

However, the thromboelastography or the thromboelastometry has problems in that they are insufficiently popular mainly because: (1) measurement is not automated and the test result depends on the technique of a measuring person, (2) it is sensitive to vibration, (3) a quality control (QC) procedure is complicated and a QC reagent is expensive, (4) interpreting an output signal (thromboelastogram) needs skills, and the like. Furthermore, since they do not show very high sensitivity to a deficiency of extrinsic or intrinsic coagulation factors, it may not satisfy the medical field's needs.

On the other hand, in recent years, as a method capable of evaluating blood coagulation measurement easily and accurately, a method for performing dielectric measurement of a blood coagulation process has been devised (Patent Documents 1 and 2). The method is to fill blood into a capacitor-like sampling unit including a pair of electrodes and the like, apply an alternating electric field thereto, and measure a change in a dielectric constant caused by the coagulation process of blood. By using the method, it is shown that coagulation and fibrinolysis reaction processes can be easily monitored (Non-Patent Literature 1).

CITATION LIST

Patent Literature

Patent Literature 1: Japanese Patent Application Laid-open No. 2010-181400 (Japanese Patent No. 5691168)
Patent Literature 2: Japanese Patent Application Laid-open No. 2012-194087 (Japanese Patent No. 5768422)

Non-Patent Literature

Non-Patent Literature 1: Y. Hayashi et al., Analytical Chemistry 87(19), 10072-10079 (2015)

DISCLOSURE OF INVENTION

Technical Problem

Excluding a perioperative period, if extrinsic or intrinsic coagulation factors are more or less deficient, it does not immediately cause hemostasis difficulty. For example, severity of hemophilia patients is classified by a deficiency of FVIII or FIX. Compared with healthy individuals, the patients including 1% or less of the factor are regarded as serious, and the patients including 5 to 40% of the factor are regarded as mild and a daily life is not interfered. On the other hand, with respect to heart surgery using a heart-lung machine or the like, it is important to take appropriate measures to determine the cause of the bleeding. Even if a deficient percentage of the coagulation factors is several tens of percent as compared with the healthy individuals, a test method that reflects the deficiency with high sensitivity is required. However, the existing comprehensive blood coagulation test has no such sensitivity. Also, quantitative measurement of each coagulation factor takes time and effort including a plasma separation and the like, and it may not satisfy the medical field's needs.

Accordingly, the present inventors have intensively studied to provide a system capable of evaluating a deficiency and/or a lowered function of extrinsic coagulation factors or intrinsic coagulation factors with high sensitivity by adding new procedures and apparatuses to the blood coagulation system analysis procedures, the apparatuses, and the like described in Patent Literature 1 and Patent Literature 2, for example, thereby completing the present technology.

Solution to Problem

Specifically, the present technology provides a blood coagulation system analysis system, including:
a blood coagulation system measurement apparatus that performs blood coagulation system measurement of a blood sample; and
a blood coagulation system analysis apparatus including
a coagulation parameter extraction unit that extracts a coagulation parameter from a measurement result by the blood coagulation system measurement apparatus, and
a blood coagulation evaluation unit that evaluates a level of blood coagulation of the blood sample on the basis of the coagulation parameter,
the measurement by the blood coagulation system measurement apparatus being performed under an extrinsic system acceleration condition and an intrinsic system acceleration condition.

The blood coagulation system analysis apparatus may further include a fibrinogen evaluation unit that evaluates a level of an amount and/or a function of fibrinogen of the blood sample on the basis of the coagulation parameter.

In addition, the blood coagulation system measurement apparatus is a blood electrical measurement apparatus that measures an electrical property of the blood sample or measures an elastic change of a coagulation clot of the blood sample.

In the electrical measurement apparatus that measures an electrical property of the blood sample, the electrical property is a dielectric constant. In addition, the coagulation parameter uses a clot time and a clot strength by the dielectric constant.

The blood coagulation system analysis system according to the present technology causes the blood coagulation evaluation unit to evaluate a level of an amount and/or a function of a coagulation factor of the blood sample on the basis of the coagulation parameter.

Furthermore, the coagulation factor is a general coagulation factor and/or a common coagulation factor and the general coagulation factor is an extrinsic system coagulation factor and/or an intrinsic system coagulation factor.

Also, the present technology provides a blood coagulation system analysis method, including the steps of:
measuring a blood coagulation system of a blood sample under an extrinsic system acceleration condition and an intrinsic system acceleration condition;
extracting a coagulation parameter from a measurement result of the blood coagulation system;
evaluating a level of blood coagulation of the blood sample on the basis of the coagulation parameter; and
evaluating a level of an amount and/or a function of fibrinogen of the blood sample on the basis of the coagulation parameter.

The blood coagulation system analysis method can analyze by using a difference between a measurement result of the blood coagulation system under the extrinsic system acceleration condition and a measurement result of the blood coagulation system under the intrinsic system acceleration condition.

Furthermore, the present technology provides a program executable by a computer, the program causing the computer to execute steps of:
extracting a coagulation parameter from a measurement result of blood coagulation system of a blood sample;
evaluating a level of blood coagulation of the blood sample on the basis of the coagulation parameter; and
evaluating a level of an amount and/or a function of fibrinogen of the blood sample on the basis of the coagulation parameter.

MODE(S) FOR CARRYING OUT THE INVENTION

Figure 1:
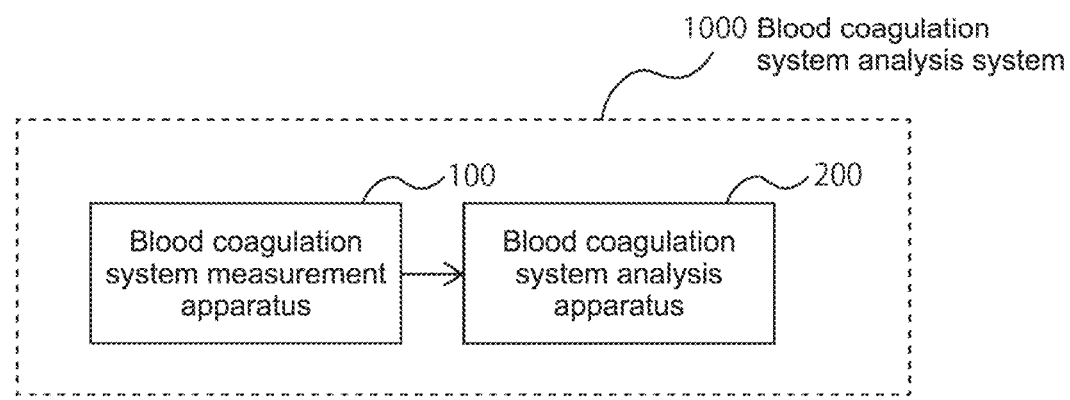
FIG. 1 is a schematic diagram showing a structure of a blood coagulation system analysis system.

Hereinafter, preferable embodiments of the present technology will be described. It should be noted that the embodiments described below illustrate typical embodiments of the present technology, and the scope of the present technology is not narrowly interpreted by the embodiments. The description will be made in the following order.
1. Blood coagulation system analysis system
 1-1. Blood coagulation system measurement apparatus
 1-2. Blood coagulation system analysis apparatus
2. First embodiment (experimental example where blood coagulation factor deficient plasma is used)
 2-1. Summary
 2-2. Experiments
 2-3. Coagulation parameter extraction
 2-4. Determination whether or not it is coagulated
 2-5. Determination whether or not amount of fibrinogen is low
 2-6. Determination that general coagulation factor is lowered or common coagulation factor is lowered
 2-7. Extrinsic system coagulation factor or intrinsic system coagulation factor lowered
 2-8. Experimental result by rotation thromboelastometry (ROTEM)
3. Second embodiment (analysis method 1 that evaluates blood coagulation factor deficiency)
 3-1. Summary
 3-2. Experiments
 3-3. Analysis
4. Third embodiment (analysis method 2 that evaluates blood coagulation factor deficiency)
 4-1. Summary
 4-2. Experiments
 4-3. Analysis
5. Fourth embodiment (experiment using VII factor (extrinsic system) deficient plasma, VIII factor (mainly, intrinsic system) deficient plasma, and sufficiently washed healthy individual red blood cells)>
 5-1. Summary
 5-2. Experiments
 5-3. Results
6. Blood coagulation system analysis program 1. Blood Coagulation System Measurement Apparatus FIG. 1 shows a blood coagulation system analysis system according to the present technology.

This system 1000 includes a blood coagulation system measurement apparatus 100 and a blood coagulation system analysis apparatus 200.

The blood coagulation system measurement apparatus 100 is not especially limited. For example, there can be used a blood electrical measurement apparatus that measures electrical properties of blood samples or a blood coagulation ability measurement apparatus that measures an elastic change of coagulation clots of the blood samples.

Specific examples of the blood electric measurement apparatus include, for example, an apparatus that performs a dielectric measurement of a blood coagulation process described in Patent Literature 1 or 2.

Specific examples of the blood coagulation ability measurement apparatus include the thromboelastography (TEG (registered trademark)) blood coagulation analysis apparatus (Haemonetics Corporation), the rotation thromboelastometry (ROTEM (registered trademark)) blood coagulation analysis apparatus (Japan Finggal Link Co., Ltd.), and the like.

The blood coagulation system analysis apparatus 200 includes a coagulation parameter extraction unit that extracts a coagulation parameter from a measurement result by the blood coagulation system measurement apparatus 100, and a blood coagulation evaluation unit that evaluates a level of blood coagulation of the blood samples on the basis of the coagulation parameter.

Figure 2:
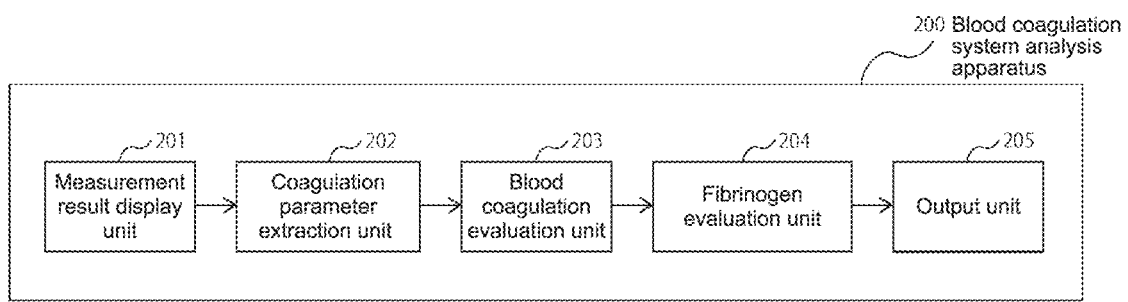
FIG. 2 is a schematic diagram showing a structure of a blood coagulation system measurement apparatus.

FIG. 2 shows a schematic diagram of the blood coagulation system measurement apparatus 200.

A measurement result display unit 201 displays a result obtained from the blood coagulation system measurement apparatus 100.

A blood coagulation parameter extraction unit 202 performs processing, e.g., makes a graph or the like, of the measurement result, and extracts a slope, a contact point, a difference, or the like of the graph, e.g., a clot time and a clot strength by a dielectric constant, appropriate to evaluate blood coagulation from the graph, as a parameter.

The blood coagulation evaluation unit 203 evaluates a level of the blood coagulation or the like on the basis of the parameter extracted from the blood coagulation parameter.

A fibrinogen evaluation unit 204 evaluates a level of an amount and/or a function of fibrinogen of the blood samples on the basis of the level of the coagulation parameter or the like.

An output unit 205 performs displaying, printing, or the like of the above result and informs a system's operator.

2. First Embodiment (Experimental Example where Blood Coagulation Factor Deficient Plasma is Used)

2-1. Summary

Figure 3:
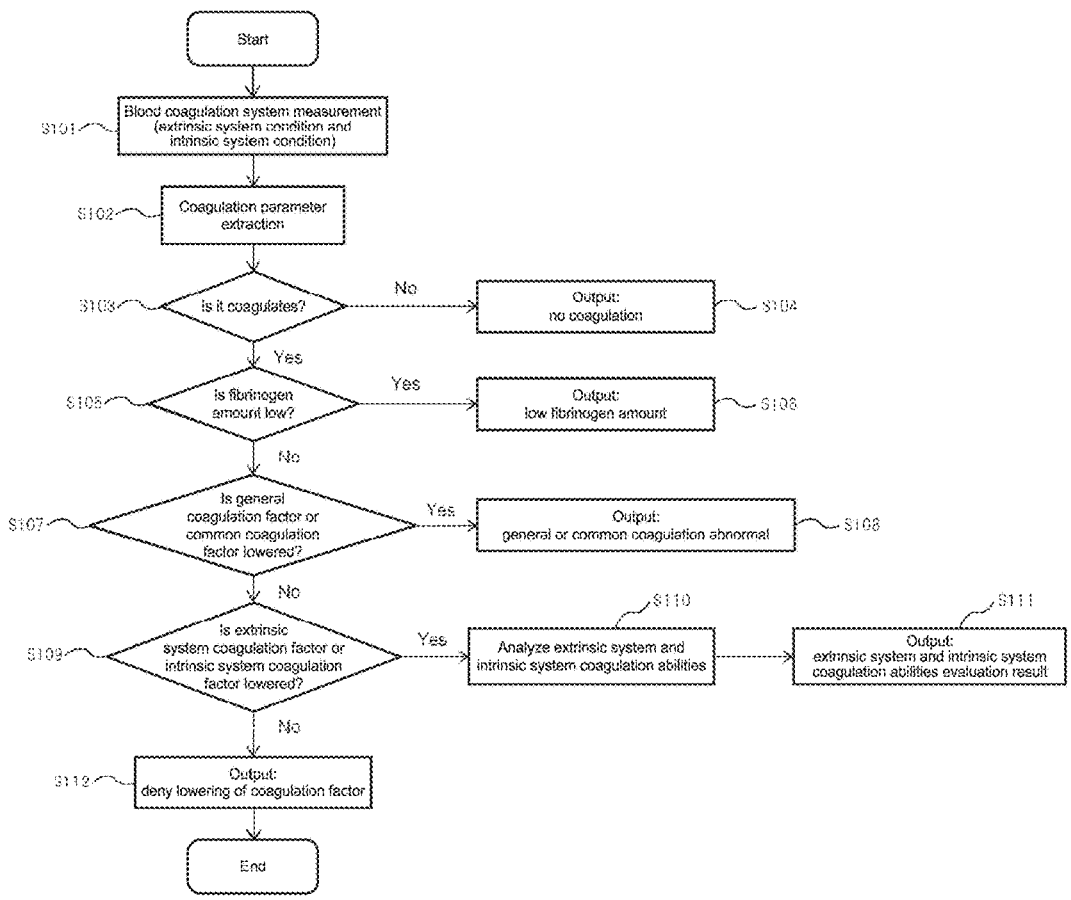
FIG. 3 is a flow chart showing from a step of measuring a blood coagulation system to a step of analyzing blood coagulation in a first embodiment.

FIG. 3 is a flow chart showing steps of this experimental example.

The experimental example starts to perform blood coagulation system measurement (S101) by at least two assays under an extrinsic system (EX) acceleration condition and intrinsic system (IN) acceleration condition.

An extrinsic system coagulation acceleration reagent used in an EX assay includes tissue thromboplastin, a tissue factor, and the like. An intrinsic system coagulation acceleration reagent used in an IN assay includes ellagic acid, kaolin, and the like.

Next, the coagulation parameter is extracted from the blood coagulation system measurement result (S102). Thereafter, a coagulation status of the blood samples is classified on the basis of the coagulation parameter. In a case where it is determined that an extrinsic system coagulation ability is lowered or an intrinsic system coagulation ability is lowered, the extrinsic system and intrinsic system coagulation abilities are analyzed in detail by additional analysis steps (S103 to S112).

Here, in order to exemplify that a deficiency status of the extrinsic system coagulation factors can be evaluated with high sensitivity by the following steps described below, FVII (extrinsic system coagulation factor) deficiency plasma was purchased, healthy individual plasma was added thereto in a different proportion, and experiments were thus performed. For comparison, rotation thromboelastometry (hereinafter also referred to as "ROTEM") was also measured.

2-2. Experiments

A spitz tube of freeze-preserved FVII factor deficient plasma (purchase) was dissolved by immersing into room temperature water and was used for preparation of a sample.

Whole blood specimens of healthy individual volunteers were drawn by using vacuum blood collection tubes including citric acid as an anticoagulant. Here, in order to prevent hemagglutination due to a blood type mismatch when mixing with the FVII factor deficient plasma, O type blood of healthy individual volunteers was drawn.

The blood was first separated into red blood cells and plasma components by a centrifuge. The red blood cells were washed with excessive PBS, were centrifuged, and a supernatant was discarded. The operation was repeated twice. To the resultant washed red blood cells, the FVII factor deficient plasma, and healthy individual plasma set aside were added. Pseudo FVII factor deficient blood was produced. Here, the proportions of the FVII factor deficient plasma and the healthy individual plasma used for sample preparation were 100:0, 95:5, 90:10, and 0:100. The four types of samples having different deficiency levels of the FVII factor were used to perform the measurement. Note that the coagulation factors that are not completely removed by the wash of the red blood cells repeated twice as described above are mixed into the samples together with the red blood cells and that several % of the FVII factor is actually present even in the samples where the proportion of the factor deficient plasma and the healthy individual plasma is 100:0.

The blood coagulation system measurement was performed for extrinsic system (hereinafter also referred to as EX) and intrinsic system (hereinafter also referred to as IN) assays by using the blood electrical measurement apparatus that measures the dielectric constant of blood. Also, the same blood samples were measured by the ROTEM (EX-TEM: extrinsic system, and IN-TEM: intrinsic system assay).

A specific procedure of measuring the dielectric constant by the blood electrical measurement apparatus is described below.

First, prepared blood samples are placed into a container (washed and dried blood collecting tube), which is set to a blood sample setting unit of the blood electrical measurement apparatus. A measurement cartridge dedicated for the blood electrical measurement apparatus in which a predetermined amount of an EX reagent (tissue factor and calcium chloride) is placed and a measurement cartridge dedicated for the blood electrical measurement apparatus in which a predetermined amount of an IN reagent (ellagic acid and calcium chloride) is placed are set to a measuring unit of the apparatus.

The measurement cartridge dedicated for the blood electrical measurement apparatus is formed by insert-molding titanium electrodes to polypropylene resin. Two opposed electrode faces function as capacitors. When blood is injected into the dedicated measurement cartridge, the blood will be filled between the electrodes. Thus, electric properties (dielectric constant) of the blood can be measured.

The measuring unit of the blood electrical measurement apparatus is temperature-controlled at 37° C., and the specimen is kept at 37° C. during the measurement. When the measurement is started by a controller (control software) of the blood electrical measurement apparatus, a predetermined amount of the blood specimen is dispensed from the blood collecting tube set to a specimen setting unit to the dedicated measurement cartridge set to the measuring unit by a dispenser (dispensing robot) built-in the apparatus. By an automatic pipetting operation, the reagent is mixed with the blood. Then, a dielectric constant change associated with the blood coagulation is measured with time and is saved in a storage, and the measurement result display unit 201 also displays the result.

2-3. Coagulation Parameter Extraction

In a case where the blood electrical measurement apparatus is used, the coagulation parameter extraction unit 202 extracts at least a clot time (hereinafter sometimes referred to as CT) and a dielectric clot strength (hereinafter sometimes referred to as DCS) from the measurement result of the dielectric constant of the blood samples (S102).

Figure 4:
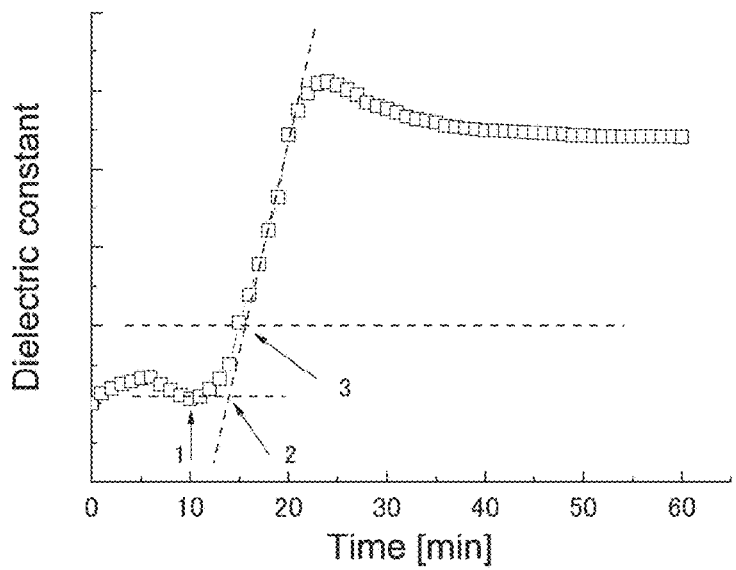
FIG. 4 is a diagram showing a method of extracting a clot time (CT) in the first embodiment.

The method is not especially limited. For example, the time that affords the minimum value (arrow 1) of the dielectric constant change at 10 MHz can be used as the CT, as shown in the graph of FIG. 4. In addition, the DCS can be calculated on the basis of a decreased width from the peak at 1 MHz. It is also possible to determine the CT with alternative methods. For example, there can be selected an intersection point of the extrapolation line (arrow 2), a threshold point (arrow 3) or the like that characterizes the dielectric constant change. Similarly, for the DCS, a width of the dielectric constant change at 10 MHz or the like may be used.

2-4. Determination Whether or not it is Coagulated

As a result of an extreme low coagulation ability, an effect of non-neutralization or the like of heparin used for treatment, or the like, the blood samples may not be coagulated. The blood coagulation evaluation unit 203 can determine the coagulation. For example, in a case where the dielectric constant does not rise in the dielectric constant change at 10 MHz, the coagulation can be determined by extremely extending the CT (S103).

In particular, in a case where the blood samples are not coagulated in both EX and IN assays, the blood samples are determined as non-coagulated blood samples (including an extreme delay of coagulation) (S104).

Figure 5:
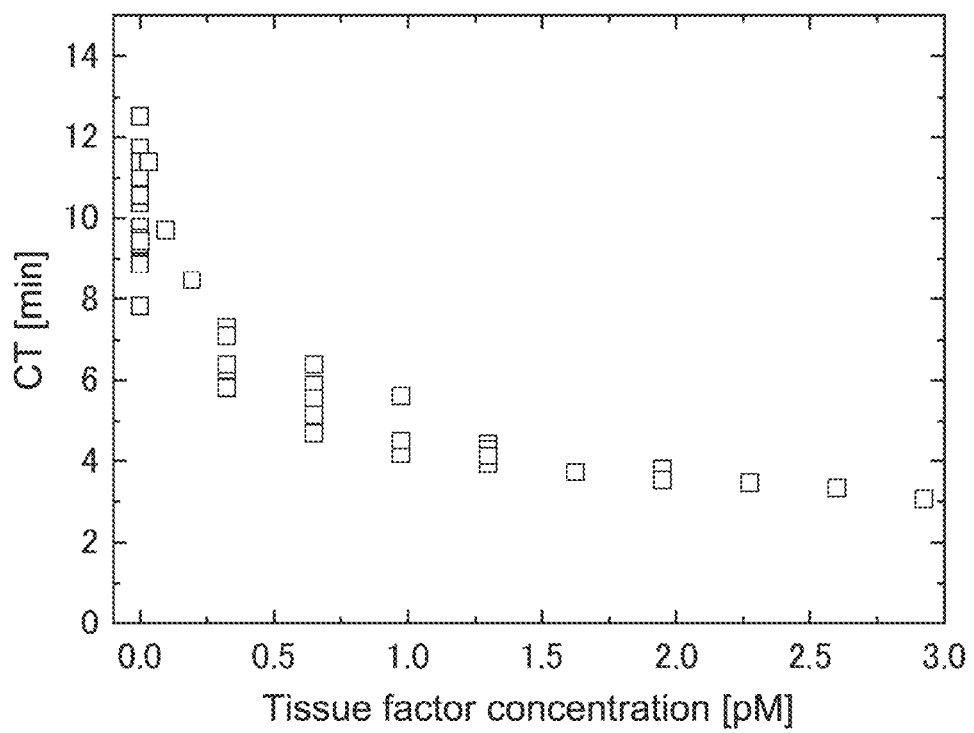
FIG. 5 is a graph showing tissue factor concentration dependency of healthy individual's blood on the clot time (CT) in the first embodiment.

Note that the CT is measured by changing a final concentration (after mixing with blood) of the tissue factor used as the reagent of the EX assay within the range of 0.3 to 3 pM, and the CT is defined as the time that affords the minimum value at 10 MHz. In this case, a separate experiment reveals that the CT of the healthy individual is eight minutes or less (FIG. 5). In addition, when the CT was measured on the tissue factor having the concentration lower than 0.3 pM, the CT was extended more or less. If no tissue factor was added, the average of the CT was 10.3±1.27 minutes. On the basis of this result, the "extreme extension of the CT" can be defined that the CT is 18 minutes or more, for example. The threshold value is provided by adding the average value of the CT where no activator such as the tissue factor is added to the healthy individual blood to a six-folded standard deviation. Also with respect to the IN assay (intrinsic system acceleration assay), the similar experiment can be performed to determine an evaluation standard (such as threshold value) of the "extreme extension of the CT".

2-5. Determination Whether or not Amount of Fibrinogen is Low

In the EX and IN assays, both of fibrin formation and platelets generally contribute to the DCS. However, if the amount of fibrinogen is extremely low and fibrin is insufficiently formed, the DCS is also low even though the platelet number and the platelet function are normal. By utilizing the finding, it is estimated that the amount of fibrinogen is low if the DCS is low in both of the EX and IN assays (S105, S106). For example, the fibrinogen evaluation unit 204 performs the determination.

In addition, more preferably, through a platelet inhibition assay (hereinafter also referred to as PI assay) that artificially and perfectly inhibits the platelet contribution, only the fibrin formation contribution can be accurately evaluated. It is effective to estimate whether or not the amount of fibrinogen is low. The PI assay can be executed by using any of (or both of) the reagents that accelerates the extrinsic system or the intrinsic system as well as a reagent that inhibits platelet coagulation such as cytochalasin D.

2-6. Determination that General Coagulation Factor is Lowered or Common Coagulation Factor is Lowered In the EX and IN assays, if it takes time until the dielectric constant reaches a certain level after the dielectric constant is changed by coagulation, a deficiency and/or a lowered function of coagulation factors may be suspected (S107). In particular, in a case where both of the EX and IN assays show the status, it assumes that the amount and/or the function of the general coagulation factors are/is generally lowered, the amount and/or the function of the common coagulation factors located downstream the coagulation reaction such as FX, prothrombin, and FV are/is lowered, or both (S108).

Figure 6:
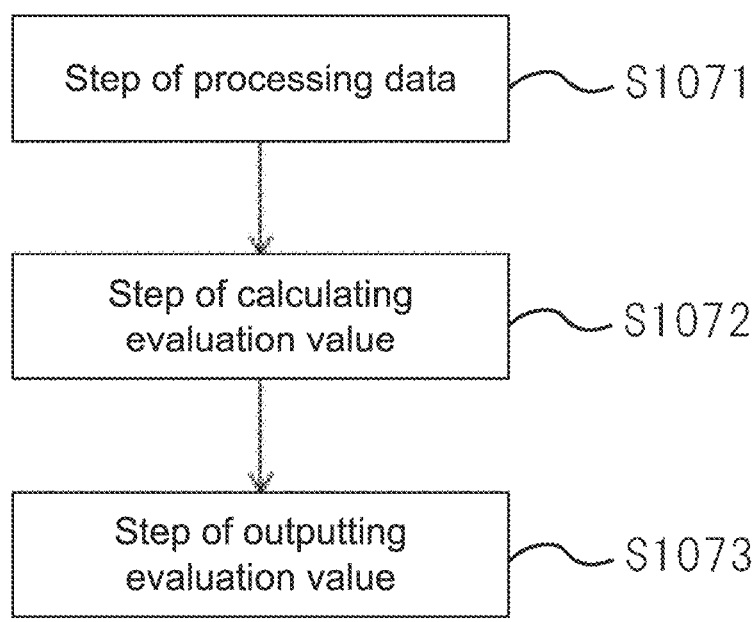
FIG. 6 is a block diagram showing steps of analyzing data of blood coagulation system measurement under extrinsic system and intrinsic system conditions in the first embodiment.

The analysis may be performed by a blood coagulation system evaluation unit 203, and can be executed by a step of processing data (S1071) in the EX and IN assays, a step of calculating an evaluation value of a level of blood coagulation (S1072), and a step of outputting the evaluation value (S1073) shown in FIG. 6. The respective steps will be described below in detail. Note that the present technology is not limited thereto.

Figure 7:
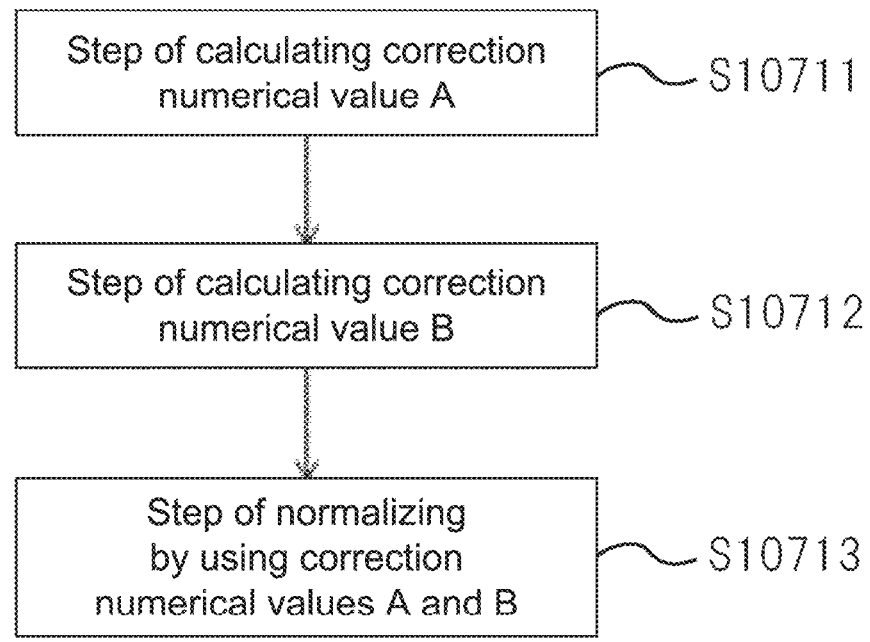
FIG. 7 is a block diagram showing steps of analyzing data of blood coagulation system measurement under the extrinsic system and intrinsic system conditions in the first embodiment.

The "step of processing data" (S1071) of FIG. 6 is a step of normalizing data, for example, and may include illustrative substeps of FIG. 7, i.e., a step of calculating a correction numerical value A (S10711), a step of calculating a correction numerical value B (S10712), and a step of normalizing by using the correction numerical values A and B (S10713).

Figure 8:
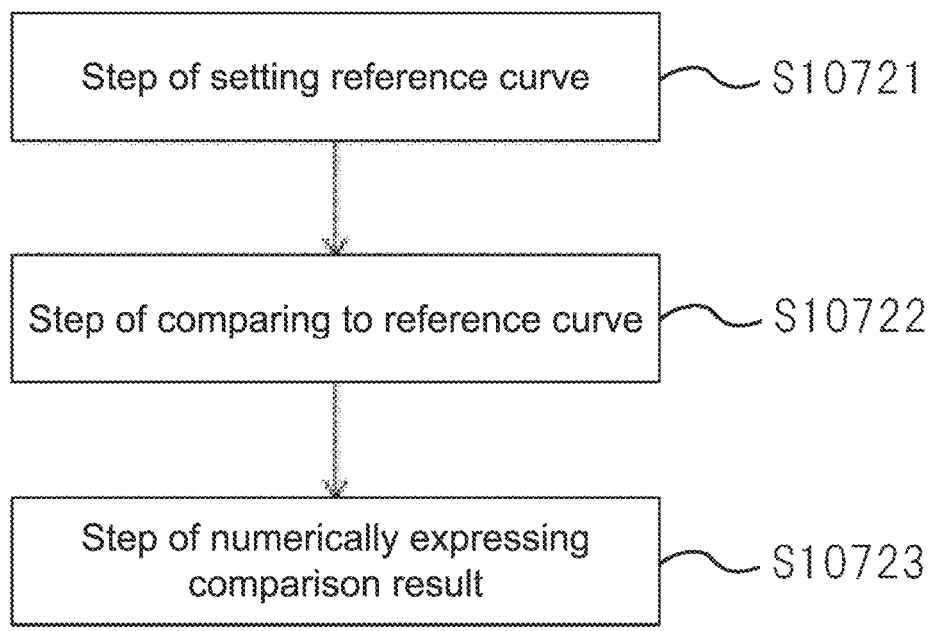
FIG. 8 is a block diagram showing steps of analyzing data of blood coagulation system measurement under the extrinsic system and intrinsic system conditions in the first embodiment.

In addition, the "step of calculating an evaluation value" (S1072) may include illustrative substeps of FIG. 8, i.e., a step of setting a reference curve (S10721), a step of comparing with the reference curve (S10722), and a step of numerically expressing a comparison result (S10723).

Hereinafter, specific examples of analysis steps shown in FIG. 6 to FIG. 8 will be described. The present technology is not limited thereto.

[Step of Processing Data] (S1071)

First, dielectric constant data ($\varepsilon$) at 10 MHz is normalized, for example. More preferably, the data is normalized (S10713) in accordance with the following Expression (1) by using two points, the minimum value ($\varepsilon_{min}$) ("correction numerical value A", S10711) and the maximum value ($\varepsilon_{max}$) ("correction numerical value B", S10712), of the dielectric constant.

[Expression 1]

$$\varepsilon_{Normalized} = (\varepsilon - \varepsilon_{min})/(\varepsilon_{max} - \varepsilon_{min}) \quad \text{Expression (1)}$$

Note that the minimum value of the dielectric constant is not necessarily selected as $\varepsilon_{min}$, and the dielectric constant at the point that the dielectric constant change (slope) is the maximum or the like can be selected, for example.

In addition, max may not be the maximum value of the dielectric constant and may also be the value of the dielectric constant after the time of a settlement of an increase of the dielectric constant (for example, after 30 minutes from the measurement start or the like), an average value therearound, or the like.

[Step of Calculating Evaluation Value] (S1072)

Next, with respect to the resultant $\varepsilon$Normalized, for example, in order to numerically express the breadth of a data rise after the CT, a difference from an imaginary curve that rises vertically at the CT (step pulse shape, for example, y=$\varepsilon$min at the zone of time t<CT, and y=max at the zone of t≥CT zone (the "step of setting reference curve", S10721)) (the "step of comparing with the reference curve", S10722), and an integral (series sum) curve ($\varepsilon$Sum) is calculated by using the following Expression (2) (the "step of numerically expressing a comparison result", S10723).

[Expression 2]

$$\text{Provided that } \varepsilon_{Sum}(n) = a \sum_{n=n_{CT}}^{n_{CT}+x} (1 - \varepsilon_{Normalized}(n)) \Delta t \quad \text{Expression (2)}$$

$$\varepsilon_{Sum}(n < n_{CT}) = 0$$

Here, "a" denotes an arbitrary scaling factor, nCT denotes a measurement point affording the CT, and Δt denotes a time (time interval) between measurement points.

Figure 9:
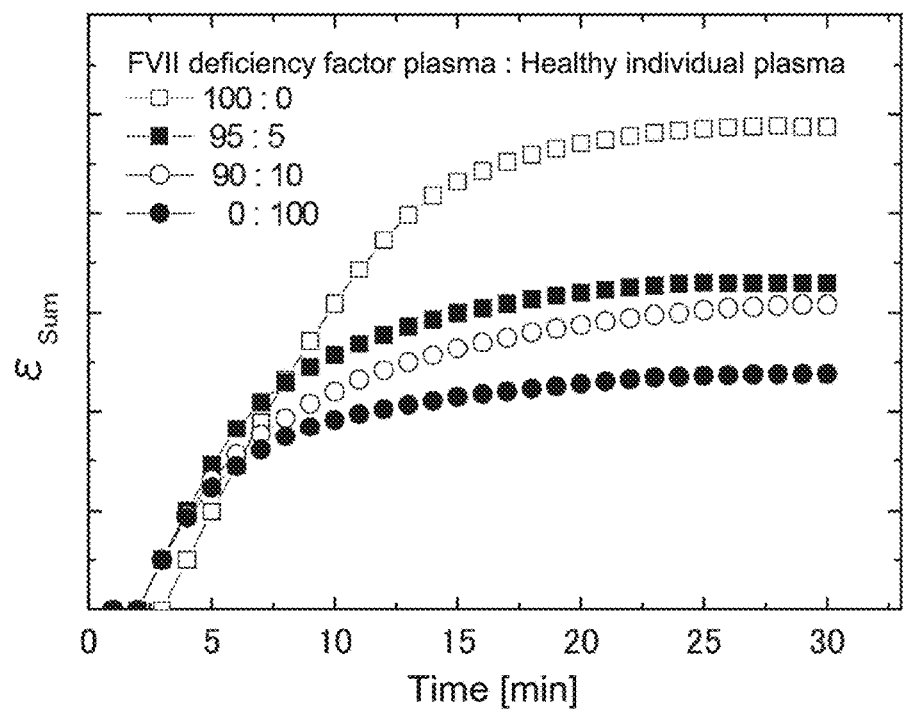
FIG. 9 is a graph showing a data analysis example of the blood coagulation system measurement in the first embodiment.

FIG. 9 exemplifies the resultant εSum. The end value of the εSum (for example, value at 30 minutes after measurement starts) is greater if the coagulation reaction slowly proceeds after the CT. In other words, it is found that the end value is sensitive to coagulation factor deficiency. Furthermore, as the shape of the (εSum) curve is changed depending on which factor is deficient, a further detailed analysis is also possible by focusing on an increase slope, a time length that the increase above a certain level is continued, or the like, for example.

Using the resultant εSum, the following determination can be performed.

If both of the εSums in the EX assay and the εSum in the IN assay have high values, it means that the coagulation reaction slowly proceeds in both of the extrinsic system and the intrinsic system. It assumes that both of the coagulation factors of the extrinsic and intrinsic systems are generally deficient, the common coagulation factors located downstream the coagulation reaction such as FX, prothrombin, and FV are deficient, or both.

2-7. Extrinsic System Coagulation Factor or Intrinsic System Coagulation Factor Lowered In the "2-6. Determination that general coagulation factor is lowered or common coagulation factor is lowered", if the εSum of either the extrinsic system or the intrinsic system is high, it can recognize that the factor of a coagulation path having the high εSum value is deficient and/or a function thereof is lowered. Also, it can recognize that both of the coagulation factors having the low εSum value and the common coagulation factors are not deficient and/or functions thereof are not lowered (S110). The result can be output as an evaluation result of the extrinsic system and/or intrinsic system coagulation (S111).

FIG. 9 is an experimental result of preparing artificially FVII-deficient samples according to the method described in the "2-2. Experiments". It is revealed that the εSum is changed in an FVII concentration-dependent manner.

In addition, if the εSums have low values both in the extrinsic system and the intrinsic system, it can deny that the coagulation factors are deficient and/or the function thereof is lowered (S112). Even in this case, if bleeding continues clinically, it can be said that the bleeding is either a surgery problem or a platelet problem.

2-8. Experimental Result by Rotation Thromboelastometry (ROTEM)

Figure 10:
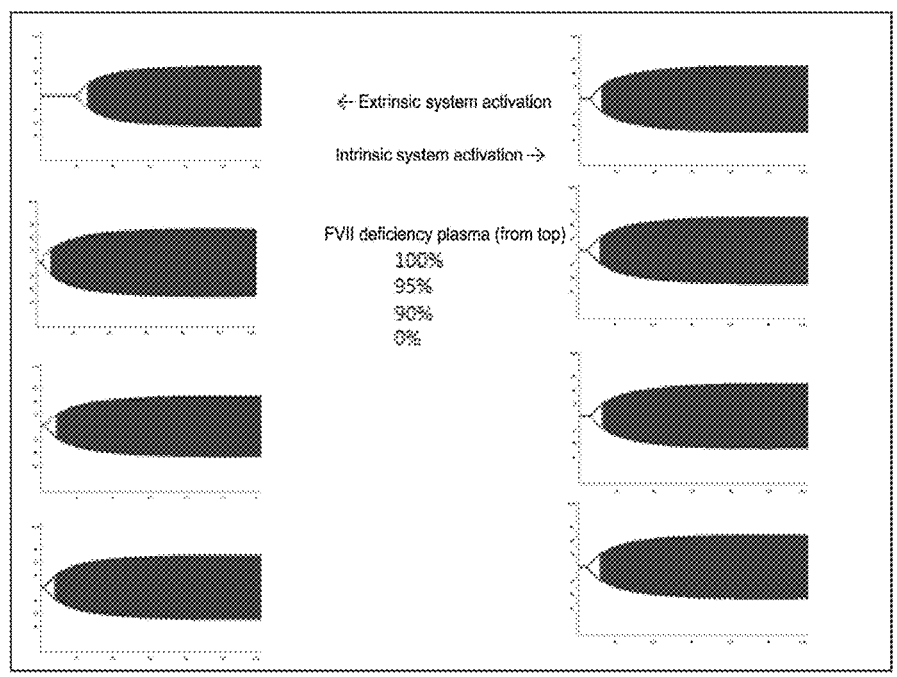
FIG. 10 is a diagram showing analyzing results of data of the blood coagulation system measurement (ROTEM) under the extrinsic system and intrinsic system conditions in the first embodiment.

FIG. 10 shows results that the same samples used in the measurement by the blood electrical measurement apparatus are measured by the ROTEM extrinsic system assay (EX-TEM) and intrinsic system assay (IN-TEM). The difference between the samples of 100% FVII factor deficient plasma and other samples can be found.

Accordingly, it becomes apparent that the blood coagulation ability measurement apparatus (ROTEM) can be used as the blood coagulation system measurement apparatus of the present technology. Considering that data visibility, sensitivity, FVII factor concentration dependency can be sensitively evaluated or the like, the blood electrical measurement apparatus that measures the electrical properties of the blood samples is more preferable.

3. Second Embodiment (Analysis Method 1 that Evaluates Blood Coagulation Factor Deficiency)

3-1. Summary

If there is a concern that either function of the extrinsic system coagulation path or the intrinsic system coagulation path is lowered, the status can be analyzed in detail by comparing the extrinsic system coagulation assay with the intrinsic system coagulation assay. In particular, it is effective to apply it to the case such that there is a concern that the extrinsic system coagulation factors are consumed by cardiac surgery involving extracorporeal circulation or the like.

3-2. Experiments

Experiments showing usability of this analysis method were performed in a procedure similar to "2-2. Experiments" of the <2. First embodiment (experimental example where blood coagulation factor deficient plasma is used).

3-3. Analysis

The analysis step is similar to that of the first embodiment. The step of "2-6. Determination that general coagulation factor is lowered or common coagulation factor is lowered" according to the first embodiment can be performed as described below.

First, according to the Expression (1), normalized curves εNormalized are acquired for the EX and IN assays, respectively. Next, with respect to the εNormalized, a difference curve (εd) between the IN assay and the EX assay is calculated. Here, in a case where the CT in the IN assay is different from the CT in the EX assay, a time axis can be corrected to provide a difference curve using the CT as reference. Then, with respect to resultant εd, an integration (series sum) curve (εdSum) is calculated as in the Expression (2).

Figure 11:
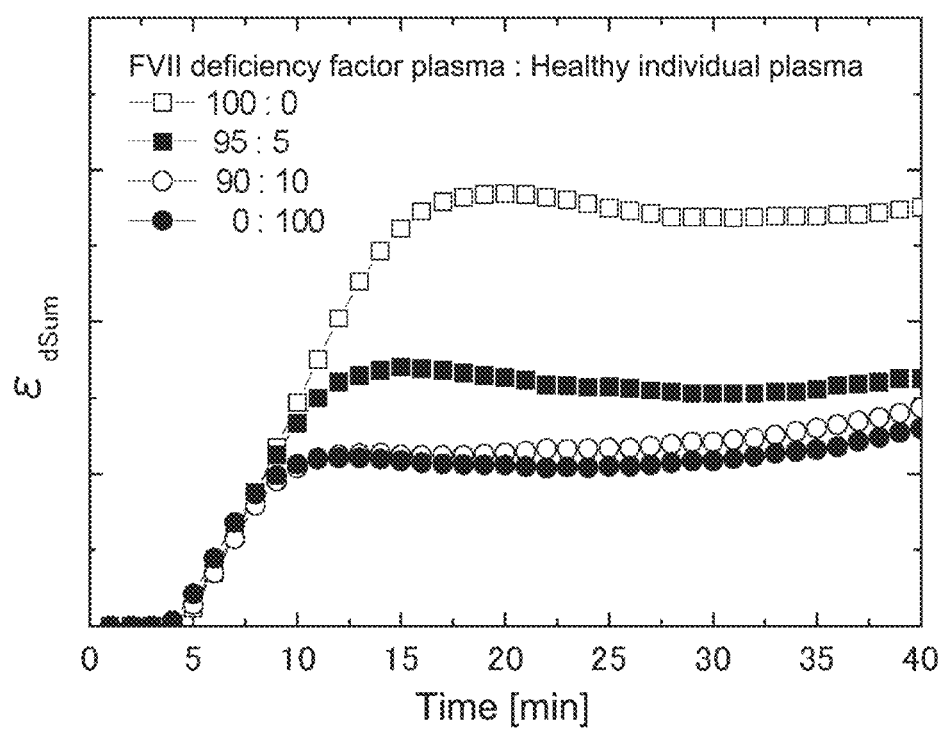
FIG. 11 is a graph showing analyzing results of blood coagulation system measurement under extrinsic system and intrinsic system conditions in a second embodiment.

FIG. 11 exemplifies the resultant experimental analysis result.

4. Third Embodiment (Analysis Method 2 that Evaluates Blood Coagulation Factor Deficiency)

4-1. Summary

A dielectric constant change associated with the blood coagulation is converted into a format capable of expressing a transient phenomenon in accordance with a series of analysis steps. The curve is Fourier (Laplace) transformed. Thus, a response characteristic to the coagulation factor deficiency or the like is analyzed at a frequency region.

4-2. Experiments

Experiments showing usability of this analysis method were performed in a procedure similar to "2-2. Experiments" of the <2. First embodiment (experimental example where blood coagulation factor deficient plasma is used).

4-3. Analysis

The analysis step is similar to that of the first embodiment. The step of "2-6. Determination that general coagulation factor is lowered or common coagulation factor is lowered" according to the first embodiment can be performed as described below.

First, according to the Expression (1), a normalized curve εNormalized is acquired.

Next, with respect to the resultant εNormalized, for example, in order to numerically express the breadth of a data rise after the CT, a difference from an imaginary curve that rises vertically at the CT is taken (δε). Here, a difference from the first embodiment is that an integral (series sum) curve is not displayed and the difference curve of each time is provided.

Figure 12:
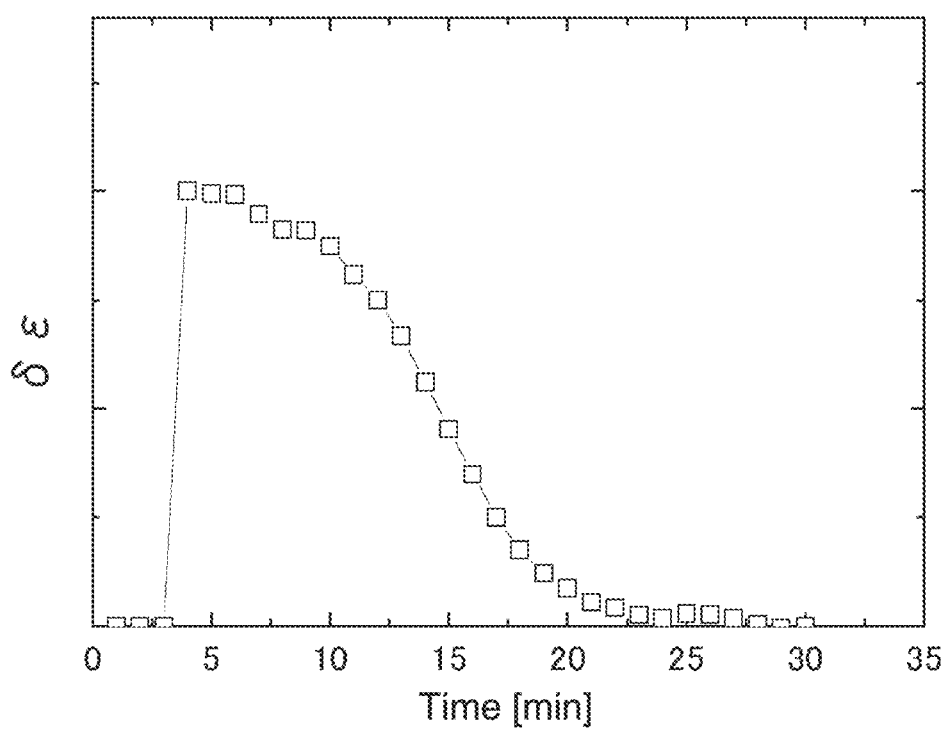
FIG. 12 is a graph showing a data analysis example of blood coagulation system measurement in a third embodiment.

FIG. 12 shows a characteristic example of the thus obtained experimental analysis result. FIG. 12 shows the character of the curve rising at the time t=CT and attenuating thereafter. The curve shape is changed depending on types of the deficient coagulation factor, for example. In order to more effectively analyze the change, the curve of FIG. 12 is regarded as a curve expressing a transient phenomenon, and is Fourier (Laplace) transformed. Thus, a spectrum of a frequency axis is provided. Depending on the types of the deficient coagulation factor, a characteristic frequency response is provided.

The above-described analysis is performed for the EX assay. The similar analysis is performed for the IN assay or the like. Furthermore, by comparing the analysis result of the EX assay with the analysis result of the IN assay, the coagulation status can be determined more accurately.

5. Fourth Embodiment (Experiment Using VII Factor (Extrinsic System) Deficient Plasma, VIII Factor (Mainly, Intrinsic System) Deficient Plasma, and Sufficiently Washed Healthy Individual Red Blood Cells)

5-1. Summary

The experiments according to the first embodiment and second embodiment used the extrinsic system coagulation factor FVII deficient plasma. In this experimental example, intrinsic system coagulation path FVIII deficient plasma was also mainly used, and a protocol of directly comparing with the FVII deficient plasma was used. In addition, in order to prevent the coagulation factors that cannot be completely removed by washing the red blood cells from mixing into the samples together with the red blood cells to the extent possible, the number of washing was increased to five times. Furthermore, a filter was used to remove platelets from the healthy individual plasma.

5-2. Experiments

Spitz tubes of freeze-preserved FVII factor deficient plasma (purchase) and FVIII factor deficient plasma (purchase) were dissolved by immersing into room temperature water and were used for preparation of samples. Whole blood specimens of healthy individual volunteers were drawn by using vacuum blood collection tubes including citric acid as an anticoagulant. Here, in order to prevent hemagglutination due to a blood type mismatch when mixing with each of factor deficient plasma, 0 type blood of healthy individual volunteers was drawn. The blood was first separated into red blood cells and plasma components by a centrifuge. The red blood cells were washed with excessive PBS, were centrifuged, and a supernatant was discarded. The operation was repeated five times.

To the resultant washed red blood cells, the FVII factor deficient plasma or the FVIII factor deficient plasma, and healthy individual plasma (platelets were removed by the filter) set aside were added. Pseudo FVII factor deficient blood and FVIII factor deficient blood were produced. Here, the proportions of the FVII factor deficient plasma and the healthy individual plasma used for sample preparation were 100:0, 95:5, and 90:10. Similarly, the proportions of the FVIII factor deficient plasma and the healthy individual plasma used for sample preparation were 100:0, 95:5, and 90:10. Furthermore, one prepared sample had the proportion of 0:100, i.e., deficient plasma was not contained. A total of seven types of samples were used to perform the measurement.

The measurement was performed for the EX and IN assays by using the blood electrical measurement apparatus. Also, the same blood samples were measured by the ROTEM (EX-TEM: extrinsic system, and IN-TEM: intrinsic system assay) which was the electrical coagulation ability measurement apparatus.

5-3. Results

Figure 13:
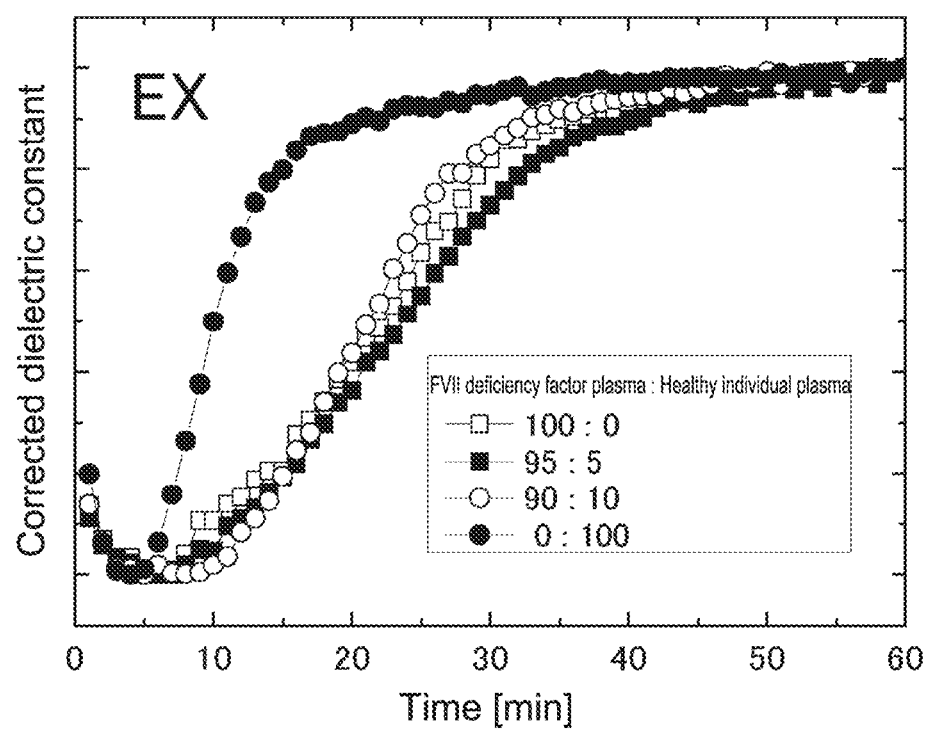
FIG. 13 is a graph showing a data analysis example of blood coagulation system measurement under extrinsic system in a fourth embodiment.
Figure 14:
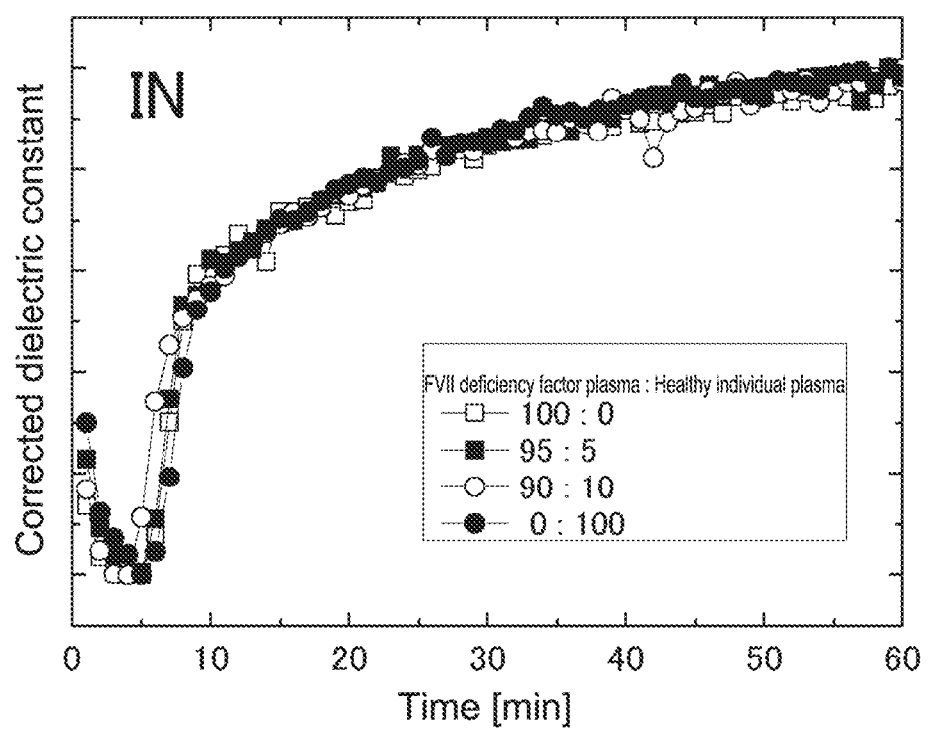
FIG. 14 is a graph showing a data analysis example of blood coagulation system measurement under intrinsic system in the fourth embodiment.
Figure 15:
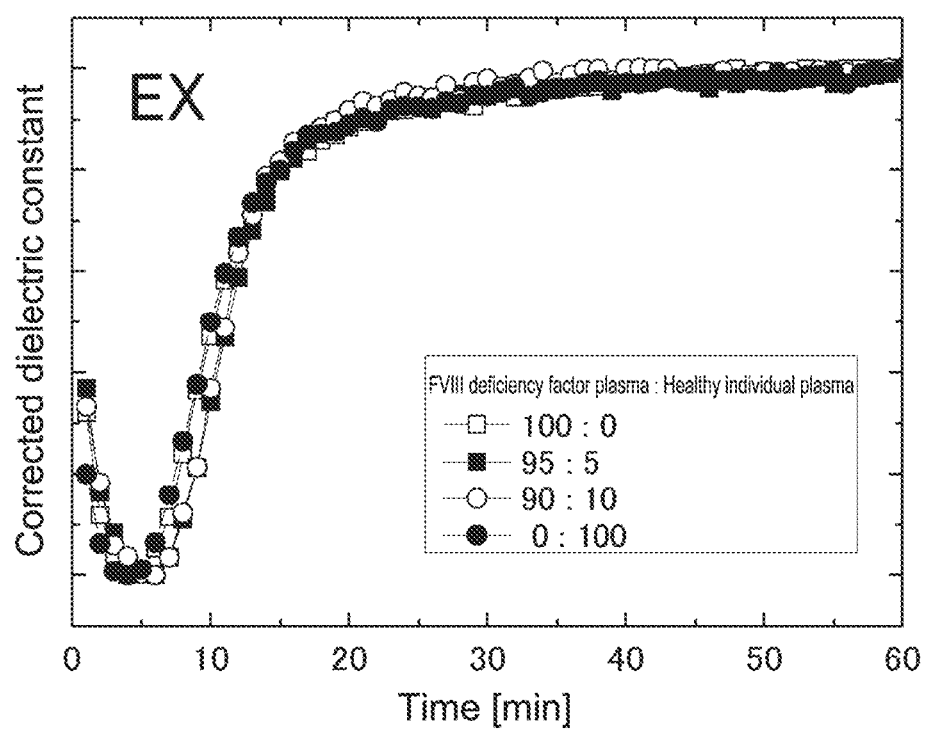
FIG. 15 is a graph showing a data analysis example of the blood coagulation system measurement under the extrinsic system in the fourth embodiment.
Figure 16:
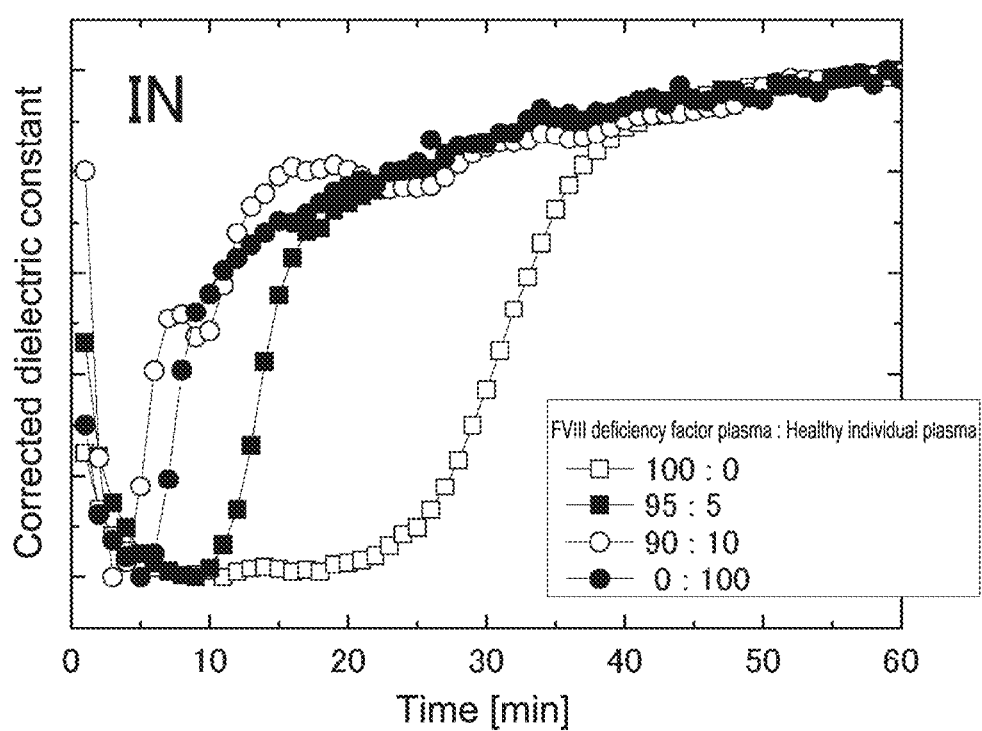
FIG. 16 is a graph showing a data analysis example of the blood coagulation system measurement under the intrinsic system in the fourth embodiment.

The measured dielectric constant was normalized according to the Expression (1). In a case where the extrinsic system coagulation factor FVII deficient plasma was used to perform the extrinsic system assay (EX), an apparent coagulation delay was observed (FIG. 13). In a case where the intrinsic system assay (IN) was performed, no coagulation delay was observed (FIG. 14). In contrast, in a case where mainly the intrinsic system coagulation factor FVIII deficient plasma was used to perform the extrinsic system assay (EX), no coagulation delay was observed (FIG. 15). In a case where the intrinsic system assay (IN) was performed, an apparent coagulation delay was observed (FIG. 16).

Thus, the results of the EX and IN assays are different depending on the types of the factor having a lowered activity. It shows that it is possible to analyze a patient's coagulation status in detail.

Furthermore, it is also possible to perform the series of analysis steps shown in the first embodiment to third embodiment on the data. It is apparent that the effects already described in the first embodiment to third embodiment can be acknowledged again.

6. Blood Coagulation System Analysis Program

The present technology provides a blood coagulation system analysis program executable by a computer, the program causing the computer to execute the analysis methods and the like in the first embodiment to fourth embodiment.

The program may be stored in a recording medium such as a magnetic disk, an optical disk, a magneto-optical disk, and a flash memory, for example, or may be distributed via a network. The program having the above-described form is executable by a personal computer externally attached to the blood coagulation system measurement apparatus or a computer built in the blood coagulation system measurement apparatus.

Note that the present technology may also have the following structures.

[1] A blood coagulation system analysis system, including:
  a blood coagulation system measurement apparatus that performs blood coagulation system measurement of a blood sample; and
  a blood coagulation system analysis apparatus including
    a coagulation parameter extraction unit that extracts a coagulation parameter from a measurement result by the blood coagulation system measurement apparatus, and
    a blood coagulation evaluation unit that evaluates a level of blood coagulation of the blood sample on the basis of the coagulation parameter,
  the measurement by the blood coagulation system measurement apparatus being performed under an extrinsic system acceleration condition and an intrinsic system acceleration condition.

[2] The blood coagulation system analysis system according to [1], in which
  the blood coagulation system analysis apparatus includes a fibrinogen evaluation unit that evaluates a level of an amount and/or a function of fibrinogen of the blood sample on the basis of the coagulation parameter.

[3] The blood coagulation system analysis system according to [1] or [2], in which
the blood coagulation system measurement apparatus is a blood electrical measurement apparatus that measures an electrical property of the blood sample or a blood coagulation ability measurement apparatus that measures an elastic change of a coagulation clot of the blood sample.
[4] The blood coagulation system analysis system according to [3], in which
the electrical property is a dielectric constant.
[5] The blood coagulation system analysis system according to [4], in which
the coagulation parameter is a clot time and a clot strength by the dielectric constant.
[6] The blood coagulation system analysis system according to any one of [1] to [5], in which
the blood coagulation evaluation unit evaluates a level of an amount and/or a function of a coagulation factor of the blood sample on the basis of the coagulation parameter.
[7] The blood coagulation system analysis system according to [6], in which
the coagulation factor is a general coagulation factor and/or a common coagulation factor.
[8] The blood coagulation system analysis system according to [7], in which
the general coagulation factor is an extrinsic system coagulation factor and/or an intrinsic system coagulation factor.
[9] A blood coagulation system analysis method, including the steps of:
measuring a blood coagulation system of a blood sample under an extrinsic system acceleration condition and an intrinsic system acceleration condition;
extracting a coagulation parameter from a measurement result of the blood coagulation system;
evaluating a level of blood coagulation of the blood sample on the basis of the coagulation parameter; and
evaluating a level of an amount and/or a function of fibrinogen of the blood sample on the basis of the coagulation parameter.
[10] The blood coagulation system analysis method according to [9], in which
analysis is performed by using a difference between a measurement result of the blood coagulation system under the extrinsic system acceleration condition and a measurement result of the blood coagulation system under the intrinsic system acceleration condition.
[11] A program executable by a computer, the program causing the computer to execute steps of:
extracting a coagulation parameter from a measurement result of blood coagulation system of a blood sample;
evaluating a level of blood coagulation of the blood sample on the basis of the coagulation parameter; and
evaluating a level of an amount and/or a function of fibrinogen of the blood sample on the basis of the coagulation parameter.

REFERENCE SIGNS LIST 100 blood coagulation system measurement apparatus
200 blood coagulation system analysis apparatus
201 measurement result display unit
202 coagulation parameter extraction unit
203 blood coagulation evaluation unit
204 fibrinogen evaluation unit
205 output unit
1000 blood coagulation system analysis system

The invention claimed is:
1. A blood coagulation system analysis system, comprising:
a blood coagulation system measurement apparatus that performs blood coagulation system measurement of a blood sample; and
a blood coagulation system analysis apparatus including
a coagulation parameter extraction unit that extracts a coagulation parameter from a measurement result by the blood coagulation system measurement apparatus, and
a blood coagulation evaluation unit that evaluates a level of blood coagulation of the blood sample on a basis of the coagulation parameter,
the measurement by the blood coagulation system measurement apparatus being performed under an extrinsic system acceleration condition using an extrinsic system coagulation acceleration reagent and an intrinsic system acceleration condition using an intrinsic system coagulation acceleration reagent different from the extrinsic system coagulation acceleration reagent.
2. The blood coagulation system analysis system according to claim 1, wherein
the blood coagulation system analysis apparatus includes a fibrinogen evaluation unit that evaluates a level of an amount and/or a function of fibrinogen of the blood sample on the basis of the coagulation parameter.
3. The blood coagulation system analysis system according to claim 1, wherein
the blood coagulation system measurement apparatus is a blood electrical measurement apparatus that measures an electrical property of the blood sample or a blood coagulation ability measurement apparatus that measures an elastic change of a coagulation clot of the blood sample.
4. The blood coagulation system analysis system according to claim 3, wherein
the electrical property is a dielectric constant.
5. The blood coagulation system analysis system according to claim 4, wherein
the coagulation parameter is a clot time and a clot strength by the dielectric constant.
6. The blood coagulation system analysis system according to claim 1, wherein
the blood coagulation evaluation unit evaluates a level of an amount and/or a function of a coagulation factor of the blood sample on the basis of the coagulation parameter.
7. The blood coagulation system analysis system according to claim 6, wherein
the coagulation factor is a general coagulation factor and/or a common coagulation factor.
8. The blood coagulation system analysis system according to claim 7, wherein
the general coagulation factor is an extrinsic system coagulation factor and/or an intrinsic system coagulation factor.
9. A blood coagulation system analysis method, comprising:
measuring a blood sample under an extrinsic system acceleration condition using an extrinsic system coagulation acceleration reagent and an intrinsic system acceleration condition using an intrinsic system coagulation acceleration reagent different from the extrinsic system coagulation acceleration reagent;
extracting a coagulation parameter from a measurement result of the blood coagulation system;

evaluating a level of blood coagulation of the blood sample on a basis of the coagulation parameter; and evaluating a level of an amount and/or a function of fibrinogen of the blood sample on the basis of the coagulation parameter.

10. The blood coagulation system analysis method according to claim 9, wherein analysis is performed by using a difference between a measurement result of the blood coagulation system under the extrinsic system acceleration condition and a measurement result of the blood coagulation system under the intrinsic system acceleration condition.

11. A non-transitory computer readable medium containing instructions that, when executed by a computer, cause the computer to perform a blood coagulation system analysis method comprising:

extracting a coagulation parameter from a measurement result of a blood sample, wherein the measurement result is obtained by a measurement performed under an extrinsic system acceleration condition using an extrinsic system coagulation acceleration reagent and an intrinsic system acceleration condition using an intrinsic system coagulation acceleration reagent different from the extrinsic system coagulation acceleration reagent;

evaluating a level of blood coagulation of the blood sample on a basis of the coagulation parameter; and evaluating a level of an amount and/or a function of fibrinogen of the blood sample on the basis of the coagulation parameter.

12. The blood coagulation system analysis system according to claim 1, wherein the blood coagulation system measurement apparatus does not include an acoustic sensor.

* * * * *